United States Patent [19]

Heerdt et al.

[11] 4,387,104
[45] Jun. 7, 1983

[54] N-SUBSTITUTED PYRUVIC ACID HYDRAZONES, PREPARATION THEREOF AND PHARMACEUTICAL COMPOSITIONS CONTAINING THEM

[75] Inventors: Ruth Heerdt, Mannheim; Hans P. Wolff, Hirschberg-Grosssachsen; Fritz Kaiser, Lampertheim; Wolfgang Schaumann, Heidelberg; Hans Kühnle, Weinheim, all of Fed. Rep. of Germany

[73] Assignee: Boehringer Mannheim GmbH, Mannheim, Fed. Rep. of Germany

[21] Appl. No.: 292,869

[22] Filed: Aug. 14, 1981

[30] Foreign Application Priority Data

Aug. 23, 1980 [DE] Fed. Rep. of Germany ....... 3031842

[51] Int. Cl.³ .................. A61K 31/195; C07C 109/12
[52] U.S. Cl. .................... 424/319; 424/309; 424/323; 560/10; 560/16; 560/34; 560/170; 560/155; 560/121; 560/125; 562/553; 562/560; 562/503; 562/505; 562/506; 562/439; 562/426; 562/427; 562/556; 564/149; 564/150; 564/148; 564/151
[58] Field of Search ............... 562/439, 426, 427, 556, 562/560, 503, 505, 553, 506; 424/309, 319, 323; 560/10, 16, 34, 170, 155, 121, 125; 564/149, 150, 148, 151

[56] References Cited

U.S. PATENT DOCUMENTS 4,206,231 6/1980 Heackel et al. ..................... 562/560

Primary Examiner—James H. Reamer
Attorney, Agent, or Firm—Sprung, Horn, Kramer & Woods

[57] ABSTRACT

A pyruvic acid hydrazone derivative of the formula:

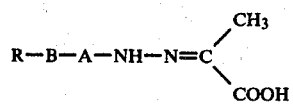

wherein
R is an aryl radical optionally substituted by lower alkyl or is an aliphatic hydrocarbon radical which can be substituted by a lower alkoxy, a cycloalkyl or an optionally substituted aryl radical,
A is an alkylene radical containing 2 to 8 carbon atoms, with at least 2 carbon atoms between B and the nitrogen atom, and
B is an oxygen or sulphur atom;
or a physiologically acceptable salt, ester or amide thereof which possesses hypoglycaemic activity.

10 Claims, No Drawings

N-SUBSTITUTED PYRUVIC ACID HYDRAZONES, PREPARATION THEREOF AND PHARMACEUTICAL COMPOSITIONS CONTAINING THEM

The present invention is concerned with N-substituted pyruvic acid hydrazones, with the preparation thereof and with pharmaceutical compositions containing them.

U.S. Pat. No. 4,206,231 describes N-substituted pyruvic acid derivatives of the general formula (I) given hereinafter, in which X represents a valency bond or a lower alkylene radical, which have an outstanding hypoglycaemic action.

Surprisingly, we have now found that the introduction of a hetero atom in the substituent X gives rise to compounds which inhibit the absorption of glucose from the intestinal tract in a dosage range at which the blood sugar-lowering action does not occur or only occurs to an insignificant extent. Therefore, the compounds can be used for the treatment of diseases in which, after ingestion of carbohydrate-containing nutriments, a very marked and long-lasting hyperglycaemia occurs. In particular, they can be used as therapeutic agents for the treatment of diabetes mellitus, prediabetes, adipositas and atherosclerosis.

Thus, according to the present invention, there are provided new pyruvic acid hydrazone derivatives of the general formula:

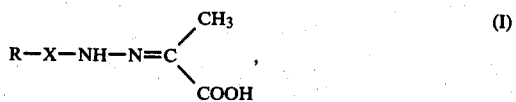

wherein R is an aryl radical optionally substituted by lower alkyl or is a straight-chained or branched, saturated or unsaturated aliphatic hydrocarbon radical, which can be substituted by a lower alkoxy, a cycloalkyl or an optionally-substituted aryl radical, X is the radical —A—B—, A being attached to the nitrogen atom and B being attached to R, A being a straight-chained or branched alkylene radical containing 2 to 8 carbon atoms, with a straight-chained part containing at least 2 carbon atoms, which connects B to the nitrogen atom and B is an oxygen or sulphur atom, and the physiologically acceptable salts, esters and amides thereof.

The aryl radical is to be understood to be an aromatic hydrocarbon radical containing 6 to 14 carbon atoms, the phenyl radical being preferred.

The aliphatic hydrocarbon radical R is straight-chained or branched, saturated or unsaturated and contains up to 5 carbon atoms and is preferably a methyl, ethyl, propyl, allyl or methallyl radical.

The term cycloalkyl radical includes carbocycles containing 5 to 7 carbon atoms, the cyclohexyl radical being preferred.

Substituted aryl radicals are to be understood to be aromatic hydrocarbon radicals containing 6 to 14 carbon atoms which are substituted by halogen atoms or lower alkyl or lower alkoxy radicals in one or more of the possible positions, the halogen atoms preferably being fluorine, chlorine or bromine.

Lower alkyl radicals are, in all cases, to be understood to be straight-chained or branched radicals containing up to 4 carbon atoms, this definition also applying to the alkyl moiety of alkoxy radicals. Preferred lower alkyl radicals include the methyl radical and preferred lower alkoxy radicals include the methoxy and ethoxy radicals.

Especially preferred straight-chained and branched alkylene radicals A are to be understood to include the following:

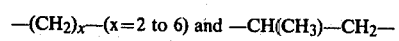

Those compounds of general formula (I) are preferred in which B is an oxygen atom.

The present invention also includes within its scope all stereoisomeric forms of the compounds of general formula (I) which can occur because of the asymmetric carbon atoms and/or double bonds (C=C, C=N) present in some of the compounds.

The compounds of general formula (I) can be prepared in conventional manner and preferably by reacting a hydrazine of the general formula:

in which R and X have the same meanings as above, with a propionic acid derivative of the general formula:

in which Y and Y' are halogen atoms or alkoxy radicals or together represent an oxygen atom and R' is a hydroxyl group, a lower alkoxy radical or an optionally substituted amino group; whereafter, if desired, the compound obtained is converted into a salt, ester or amide or wherein, if desired, a free acid is liberated from a derivative thereof.

Halogen in the substituents Y and Y' in compounds of general formula (III) means fluorine, bromine, chlorine or iodine, chlorine and bromine being preferred. Alkoxy radicals Y, Y' and R' contain up to 4 carbon atoms, the methoxy and ethoxy radicals being preferred.

In carrying out this process, a substituted hydrazine (II) or an appropriate salt thereof is reacted in an appropriate polar solvent, for example water, a lower alcohol or acetic acid, with a propionic acid derivative (III) or preferably with a salt thereof and, optionally with the help of a buffer, for example sodium acetate, brought to a weakly acidic pH value. The reaction takes place at ambient temperature but can also be carried out with heating. The hydrazones (I) can be filtered off from the reaction medium as sparingly soluble compounds or can be extracted with appropriate solvents, for example, non-polar solvents.

It is also possible to carry out the complete synthesis in a one-pot process by first preparing the substituted hydrazine (II) from an amine by reaction with hydroxylamine O-sulphonic acid and then, after the addition of the propionic acid derivative (III), to precipitate out the desired hydrazone (I).

Some of the substituted hydrazines and the salts thereof are new compounds. However, they can be prepared by known processes, for example by reacting hydrazine with appropriate alkyl halides. In general, it is not necessary to prepare them in pure form so that the crude products obtained can be employed.

The physiologically acceptable salts are preferably the alkali metal, alkaline earth metal and ammonium salts, as well as possibly salts with blood sugar-lowering biguanides. The salts may be prepared in conventional manner, for example by reacting the compounds (I) with free bases, carbonates or alcoholates.

When esters are obtained as intermediates in the above-described process, they can be isolated or possibly saponified directly to give the corresponding carboxylic acids. On the other hand, when carboxylic acids are obtained, they can, again according to conventional methods, be reacted to give the desired esters. Saponification of the esters is preferably carried out in an alkaline medium.

The esters of the carboxylic acids of general formula (I) are, within the meaning of the present invention, in principle to be understood to be the reaction products of the carboxylic acids with alcohols, the preferred alcohols being the lower monohydroxy alcohols, such as methanol, ethanol, n-propanol and isopropanol.

The amides of general formula (I) according to the present invention can be prepared in conventional manner from the carboxylic acids or from reactive derivatives thereof by reaction with amines. The amine components can be, for example, ammonia and mono- and dialkylamines, as well as amino acids, amongst which there may be mentioned, for example, p-aminobenzoic acid, anthranilic acid, phenylalanine, α- and β-alanine, serine, valine, glycine, arginine and many others.

As anti-diabetic compositions according to the present invention, there can be considered all conventional oral and parenteral forms of administration, for example, tablets, capsules, dragees, syrups, solutions, suspensions, drops, suppositories and the like. For this purpose, the active material is mixed with solid or liquid carrier materials and subsequently brought into the desired form. Solid carrier materials include, for example, starch, lactose, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

As injection medium it is preferred to use water which contains the additives conventional in the case of injection solutions, such as stabilizing agents, solubilizing agents and/or buffers. Additives of this kind include, for example, acetate and tartrate buffers, ethanol, complex formers (such as ethylenediamine-tetraacetic acid and the non-toxic salts thereof) and high molecular weight polymers (such as liquid polyethylene oxide) for viscosity regulation.

For combating diseases in which, after the ingestion of carbohydrate-containing nutriments, a very marked and long-lasting hyperglycaemia occurs, the pharmacologically-active compounds according to the present invention are employed in individual doses of 1 to 600 and preferably of 50 to 500 mg., these individual doses being administered, according to need, one or more times daily.

Apart from the compounds mentioned in the specific examples and also all the other possible combinations of the individual definitions of the substituents R, X, A and B, the following acid is also preferred: 2-[2-(β-methylcinnamyloxy)-ethylhydrazono]-propionic acid.

The following examples are given for the purpose of illustrating the present invention:

EXAMPLE 1

2-(2-p-Tolyloxyethylhydrazono)-propionic acid 11.8 g. (58 mmol) 2-p-Tolyloxyethylhydrazine hydrochloride are dissolved in 100 ml. water and mixed, while stirring at ambient temperature, with a solution of 5.1 g. (58 mmol) pyruvic acid and 7.5 g. sodium acetate in 35 ml. water. An oil thereby separates out which, after decanting off the aqueous reaction phase, is brought to crystallization by triturating with water. The crystals are filtered off with suction, dissolved in water by the addition of 30 ml. 2 N aqueous sodium hydroxide solution and the solution slowly mixed with 2 N hydrochloric acid. The precipitate obtained is filtered off with suction and dried. There are obtained 8.9 g. (65% of theory) 2-(2-p-tolyloxyethylhydrazono)-propionic acid; m.p. 57°–59° C.

The following compounds are obtained in an analogous manner by reacting pyruvic acid:

(a) with 2-(2-ethoxyethoxy)-ethylhydrazine sulphate: 2-[2-(2-ethoxyethoxy)-ethylhydrazono]-propionic acid; m.p. 51°–55° C.

(b) with 2-phenoxyethylhydrazine hydrochloride: 2-(2-phenoxyethylhydrazono)-propionic acid m.p. 90°–92° C. (recrystallized from isopropanol-water) (hydrate)

(c) with 3-phenoxypropylhydrazine hydrochloride: 2-(3-phenoxypropylhydrazono)-propionic acid m.p. 56°–58° C. (recrystallized from isooctane-toluene) (hydrate)

EXAMPLE 2

Sodium 2-(2-phenoxypropylhydrazono)-propionate 14.6 g. (72 mmol) 2-Phenoxypropylhydrazine hydrochloride are dissolved in 100 ml. water and mixed with a solution of 6.7 g. (76 mmol) pyruvic acid and 14 g. sodium acetate in 30 ml. water, an oil thereby being formed. After stirring for about 1 hour, the oil is extracted with methylene chloride, the solution is washed with water, dried with anhydrous sodium sulphate and the methylene chloride distilled off in a vacuum. The oily residue is dissolved in 50 ml. ethanol and 13.4 ml. of a 30% sodium methylate solution added thereto, while stirring. Sodium 2-(2-phenoxypropylhydrazono)-propionate precipitates out and is filtered off with suction, first washed with a little ethanol and then with diethyl ether. The yield is 11.3 g. (61% of theory); m.p. 209°–211° C.

The following compounds are obtained in an analogous manner by reacting pyruvic acid:

(a) with 2-(2-methoxyethoxy)-ethylhydrazine sulphate and subsequent preparation of the sodium salt: sodium 2-[2-(2-methoxyethoxy)-ethylhydrazono]-propionate m.p. 175°–177° C.

(b) with 2-benzyloxyethylhydrazine hydrochloride and subsequent preparation of the sodium salt sodium 2-(2-benzyloxyethylhydrazono)-propionate m.p. 175° C. (hemihydrate)

(c) with 2-allylthioethylhydrazine hydrochloride and subsequent preparation of the sodium salt sodium 2-(2-allylthioethylhydrazono)-propionate m.p. 197° C. (decomp.)

(d) with 2-phenylthioethylhydrazine hydrochloride and subsequent preparation of the sodium salt sodium 2-(2-phenylthioethylhydrazono)-propionate m.p. 199°–200° C.

EXAMPLE 3

2-(2-Allyloxyethylhydrazono)-propionic acid 4.0 g. (34 mmol) 2-Allyloxyethylhydrazine are dissolved in 20 ml. water and mixed with 3.1 g. (36 mmol) pyruvic acid. The reaction mixture is left to stand for about 30 minutes and then extracted with diethyl ether. The ethereal extracts are washed with a sodium acetate-hydrochloric acid buffer solution (pH 3.5), dried with anhydrous sodium sulphate and evaporated in a vacuum at ambient temperature. The residue obtained is a colorless oil. There are obtained 3.2 g. (50% of theory) 2-(2-allyloxyethylhydrazono)-propionic acid.

NMR spectrum (d$_6$ DMSO)

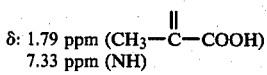

δ: 1.79 ppm (CH$_3$—C—COOH)
7.33 ppm (NH)

The following compounds are obtained in an analogous manner by reacting pyruvic acid:

(a) with 6-methoxyhexylhydrazine: 2-(6-methoxyhexylhydrazono)-propionic acid, colorless oil.

NMR spectrum (d$_6$ DMSO)

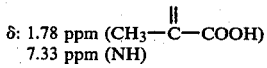

δ: 1.78 ppm (CH$_3$—C—COOH)
7.33 ppm (NH)

(b) with 5-ethoxypentylhydrazine: 2-(5-ethoxypentylhydrazono)-propionic acid, colorless oil.

NMR spectrum (d$_6$ DMSO)

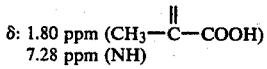

δ: 1.80 ppm (CH$_3$—C—COOH)
7.28 ppm (NH)

(c) with 4-propoxybutylhydrazine: 2-(4-propoxybutylhydrazono)-propionic acid, colorless oil.

NMR spectrum (d$_6$ DMSO)

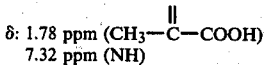

δ: 1.78 ppm (CH$_3$—C—COOH)
7.32 ppm (NH)

(d) with 2-(2-cyclohexylethoxy)-ethylhydrazine: 2-[2-(2-cyclohexylethoxy)-ethylhydrazono]-propionic acid, colorless oil.

NMR spectrum (d$_6$ DMSO)

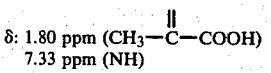

δ: 1.80 ppm (CH$_3$—C—COOH)
7.33 ppm (NH)

(e) with 3-benzyloxypropylhydrazine: 2-(3-benzyloxypropylhydrazono)-propionic acid, colorless oil.

NMR spectrum (d$_6$ DMSO)

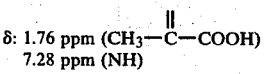

δ: 1.76 ppm (CH$_3$—C—COOH)
7.28 ppm (NH)

(f) with 2-(2-(2-methoxyethylthio)-ethylhydrazine: 2-[2-(2-methoxyethylthio)-ethylhydrazono]-propionic acid, colorless oil.

NMR spectrum (d$_6$ DMSO)

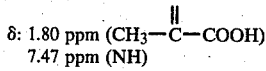

δ: 1.80 ppm (CH$_3$—C—COOH)
7.47 ppm (NH)

The novel compounds may be administered by themselves or in conjunction with carriers which are pharmacologically acceptable, either active or inert. The dosage units are about 0.2 to 2 grams per day for an adult or about 3–30 mg/kg per day although higher or lower dosages can be used. Rather than a single dose it is preferable if the compounds are administered in the course of a day, i.e. about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50–500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diamine-tetraacetic acid), high molecular weight polymers (such as liquid polyethylene oxide) for viscosity regulation or polyoxyethylene derivatives of sorbitan anhydrides.

Solid carrier materials include, for example, starch lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

As noted hereinabove the material administered may be the acid or a salt, ester or amide thereof. It is believed that due to hydrolysis in the body the active material is in all these instances the same, viz. probably the acid.

To establish the pharmacological properties of the compounds in accordance with the invention, blood-sugar-lowering activity and resorption inhibition were determined in separate tests and compared with two structurally related compounds.

1. Test procedure for determination of the threshold dose

Fasting guinea pigs were used as experimental model to determine the threshold dose of the blood-lowering activity of the substances to be investigated. Food was withheld from the individual animals used in the investigation for 16 hours prior to the start of the tests. The animals were kept unfed throughout the testing period but had free access to drinking water.

The substances were administered through intraperitoneal injection of a solution of the potassium salt at pH 7.4.

A control group carried along in parallel was given an 0.9% NaCl solution.

The drawing of blood for determination of the glucose concentrations was effected immediately prior to administration of the substances and at one-hour intervals up to the fourth hour after the administration of the substances. To this end, an ear vein was carefully punctured with a No. 18 cannula, and the drops of blood issuing were picked up with a 10 μl capillary.

The blood-glucose concentration was determined in the hemolysate by the specific hexokinase method. To this end, the 10 μl blood sample was pipetted into a stabilizer solution containing digitonin as hemolysis accelerator and maleinimide as glycolysis inhibitor. Following this, an aliquot was taken from the hemolysate so obtained and determined by the hexokinase method on an LKB 8600 (made by LKB, Bromma, Sweden).

The dose which with the specified number of test animals per dose group (N=4) was just large enough to produce a significant lowering of fasting glycemia ($p<0.05$) was adopted as threshold dose.

2. Test procedure for determination of resorption-inhibiting activity

To determine the effect on glucose resorption, oral glucose loading was effected. To this end, the substance to be tested was administered intraperitoneally as potassium salt, as described, to a group of ten fasting guinea pigs. At the same time, 1 g glucose was orally administered to the animals as a 20% solution by means of an esophageal bougie.

After a preliminary value has been established, up to 200 ml blood was taken from the animals at close (20-minute) intervals for determination of the glucose concentrations, as described.

A control group carried along in parallel also was given 1 g glucose p.o., and intraperitoneally a corresponding amount of 0.9% NaCl solution.

The blood-glucose concentration was determined in the hemolysate by the hexokinase method, as described.

With regard to glucose resorption, the area under the concentration/time curve, calculated by means of the empirical trapeze formula, served as quantity to be measured. The difference in the area between the control and test groups, expressed in percent, was used as a measure for the inhibition of glucose resorption.

The following compounds were tested as reference substances:

(A) 2-(phenethylhydrazono)-propionic acid (Example 1 from U.S. Pat. No. 4,136,196)
(B) 2-(2-cyclohexylethylhydrazono)-propionic acid (Example 1 from U.S. Pat. No. 4,206,231)

The results are presented in the following table:

TABLE

| Example No. | Threshold dose Guinea pig (mg/kg) i.p. | Resorption inhibition Dose (mg/kg) i.p. | % inhibition |
|---|---|---|---|
| A | 10–15 | 10 | 0 |
| B | 15 | 15 | 0 |
| 1 | 25 | 40 | 25 |
| 1b | 25 | 40 | 98 |
| 2a | >50 | 40 | 37.03 |
| 2b | >50 | 40 | 49.86 |
| 2c | 10–25 | 10 | 16 |
| 2d | 25–50 | 40 | 33 |
| 3 | 25 | 20 | 9 |
| 3a | 20 | 20 | 11 |
| 3b | 20–25 | 20 | 34 |
| 3d | >50 | 40 | 15 |
| 3e | >50 | 40 | 44 |
| 3f | 25 | 20 | 17.3 |

It will be understood that the specification and examples are illustrative but not limitative of the present invention and that other embodiments within the spirit and scope of the invention will suggest themselves to those skilled in the art.

We claim:

1. A pyruvic acid hydrazone derivative of the formula:

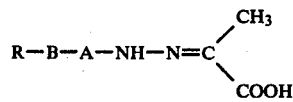

wherein
R is an aromatic hydrocarbon radical containing 6 to 14 carbon atoms optionally substituted by lower alkyl or an aliphatic hydrocarbon radical which can be substituted by a lower alkoxy, by a cycloalkyl or by an aromatic hydrocarbon radical containing 6 to 14 carbon atoms and optionally substituted by halogen or by lower alkyl or lower alkoxy,
A is an alkylene radical containing 2 to 8 carbon atoms, with at least 2 carbon atoms between B and the nitrogen atom, and
B is an oxygen or sulphur atom;
or a physiologically acceptable salt, ester or amide thereof.

2. A pyruvic acid hydrazone derivative according to claim 1,
wherein
R is an aromatic hydrocarbon radical containing 6 to 14 carbon atoms optionally substituted by lower alkyl or is an hydrocarbon radical containing up to 5 carbon atoms optionally substituted by methoxy, ethoxy, cycloalkyl of 5 to 7 carbon atoms or aromatic hydrocarbon containing 6 to 14 carbon atoms and optionally substituted by halogen, $C_{1-4}$-alkyl, or $C_{1-4}$-alkoxy, and A is —$(CH_2)_{2-6}$— or —$CH(CH_3)$—$CH_2$—.

3. A compound according to claim 1, wherein such compound is 2-(3-phenoxypropylhydrazono)-propionic acid of the formula

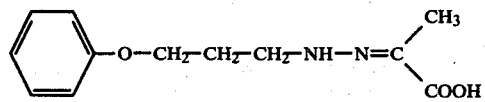

or a physiologically compatible salt, lower alkyl ester or amide thereof.

4. A compound according to claim 1, wherein such compound is 2-[2-(2-methoxyethoxy)-ethylhydrazono]-propionic acid of the formula

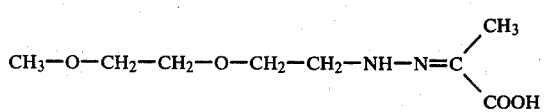

or a physiologically compatible salt, lower alkyl ester or amide thereof.

5. A compound according to claim 1, wherein such compound is 2-(2-benzyloxyethylhydrazono)-propionic acid of the formula

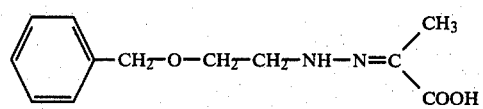

or a physiologically compatible salt, lower alkyl ester or amide thereof.

6. A compound according to claim 1, wherein such compound is 2-(5-ethoxypentylhydrazono)-propionic acid of the formula

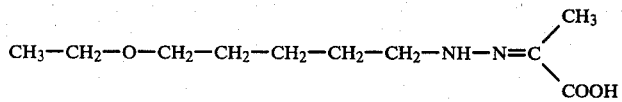

or a physiologically compatible salt, lower alkyl ester or amide thereof.

7. A compound according to claim 1, wherein such compound is 2-[2-(2-methoxyethylthio)-ethylhydrazono]-propionic acid of the formula

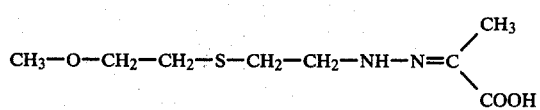

or a physiologically compatible salt, lower alkyl ester or amide thereof.

8. A hypoglycaemic composition of matter comprising a hypoglycaemically active amount of a compound according to claim 1 or a salt, lower alkyl ester or amide thereof in admixture with a diluent.

9. A method of lowering the blood sugar level of a patient comprising administering to such patient a hypoglycaemically active amount of a compound according to claim 1 or a salt, lower alkyl ester or amide thereof.

10. The method according to claim 9, wherein there is administered
2-(3-phenoxypropylhydrazono)-propionic acid,
2-[2-(2-methoxyethoxy)-ethyl-hydrazono]-propionic acid,
2-(2-benzyloxyethylhydrazono)-propionic acid,
2-(5-ethoxypentylhydrazono)-propionic acid, or
2-[2-(2-methoxyethylthio)-ethylhydrazono]-propionic acid,
or a physiologically compatible salt, lower alkyl ester or amide thereof.

* * * * *